United States Patent [19]

Siiman et al.

[11] Patent Number: 5,240,640

[45] Date of Patent: * Aug. 31, 1993

[54] IN SITU USE OF GELATIN OR AN AMINODEXTRAN IN THE PREPARATION OF UNIFORM FERRITE PARTICLES

[75] Inventors: Olavi Siiman, Davie; Alexander Burshteyn, Miami Lakes, both of Fla.

[73] Assignee: Coulter Corporation, Hialeah, Fla.

[*] Notice: The portion of the term of this patent subsequent to Nov. 5, 2008 has been disclaimed.

[21] Appl. No.: 786,024

[22] Filed: Oct. 31, 1991

Related U.S. Application Data

[63] Continuation-in-part of Ser. No. 532,434, Jun. 4, 1990, Pat. No. 5,062,991.

[51] Int. Cl.$^5$ .......................... B01J 13/10; H01F 1/36
[52] U.S. Cl. .............................. 252/315.2; 252/62.51; 252/62.53; 252/62.54; 252/309; 252/313.1; 427/213.3; 428/402; 428/403; 436/526
[58] Field of Search ................. 252/309, 313.1, 315.2, 252/62.51, 62.53, 62.54; 427/213.3; 428/402, 403

[56] References Cited

U.S. PATENT DOCUMENTS

| | | | |
|---|---|---|---|
| 3,047,429 | 7/1962 | Stoller et al. | 252/62.53 X |
| 4,115,534 | 9/1978 | Ithakissios | 252/62.53 X |
| 4,358,388 | 11/1982 | Daniel et al. | 252/62.54 |
| 4,452,773 | 6/1984 | Molday | 424/1.1 |
| 4,554,088 | 11/1985 | Whitehead et al. | 252/62.54 |
| 4,795,698 | 1/1989 | Owen et al. | 435/4 |
| 4,810,401 | 3/1989 | Mair et al. | 252/62.56 |
| 4,965,007 | 10/1990 | Yudelson | 252/62.53 |
| 5,062,991 | 11/1991 | Siiman et al. | 252/315.2 |
| 5,076,950 | 12/1991 | Ullman et al. | 252/62.51 |

FOREIGN PATENT DOCUMENTS 8805337 7/1988 PCT Int'l Appl. .

OTHER PUBLICATIONS

R. Bendaoud et al., *Trans. On Magnetics*, MAG-23, 3869-3873 (1987).
T. Sugimoto et al., *J. Coll. Interface Sci.*, 74:227-243 (1980).
H. Tamura et al., *J. Coll. Interface Sci.*, 90:100 (1982).
A. Regazzoni et al., *Corrosion*, 38:212 (1982).
A. Regazzoni et al., *Colloids & Surfaces*, 6:189 (1983).
E. Matijevic, J. Coll. & Interface Sci., 117:593 (1987).
P. H. Hess et al., *J. App. Poly Sci.*, 10:1915-1927 (1966).

*Primary Examiner*—Richard D. Lovering
*Attorney, Agent, or Firm*—Silverman, Cass & Singer, Ltd.

[57] ABSTRACT

A method is described for the preparation of uniform colloidal particles of ferrites, containing manganese(II), at a relatively low temperature in the presence of an aminodextran solution which acts as a support vehicle for the nucleation and growth of colloidal particles of metal oxide and for dispersion as separate single particles.

9 Claims, 2 Drawing Sheets

IN SITU USE OF GELATIN OR AN AMINODEXTRAN IN THE PREPARATION OF UNIFORM FERRITE PARTICLES

RELATED INVENTION

This application is a Continuation-In-Part of Ser. No. 07/532,434 filed Jun. 4, 1990, now U.S. Pat. No. 5,062,991, for "IN SITU USE OF GELATIN IN THE PREPARATION OF UNIFORM FERRITE PARTICLES".

FIELD OF THE INVENTION

This invention relates generally to a method for the preparation of metal oxide particles. More specifically, this invention is directed to an improved method for preparing uniform colloidal ferrite particles containing manganese(II), zinc(II), mixed manganese(II)-zinc(II), iron(II), barium(II), cobalt(II) or nickel(II). The particles of this invention are formed at a relatively low temperature in the presence of gelatin which acts as a vehicle for their nucleation and growth and for their dispersion into separate single particles of uniform size and shape.

BACKGROUND OF THE INVENTION

The invention is directed to overcoming the problem associated with obtaining well-dispersed colloidal particles of uniform size and shape of ferrites containing manganese(II), zinc(II), mixed manganese(II)-zinc(II), iron(II), barium(II), cobalt(II) or nickel(II). Colloidal particles of manganese(II) and zinc(II) or mixed manganese(II)-zinc(II) ferrites of uniform shape and size have not previously been reported. The invention provides a method of preparation of magnetic metal oxide particles in the presence of a polymer, solubilized in an aqueous medium wherein the colloidal particles of ferrites containing manganese(II), zinc(II), mixed manganese(II)-zinc(II), iron(II), barium(II), cobalt(II) and nickel(II), are of a well-defined and uniform shape and size and are dispersed as single particles in an aqueous media.

Ferrites containing manganese and/or zinc in fine particle form represent an important class of ferrimagnetic materials. Most preparations of manganese ferrites have been carried out at high temperatures (1000-2000° C.) from solid solutions to produce large crystallites [German Patent, DE 3619746 A1, Japanese Patents, JP 8791423 A2 and JP8791424 A2]. Lower temperature (350° C.) decomposition of a mixed Mn-Fe oxalate, followed by reduction with $H_2/H_2O$, gave a polycrystalline powder which was characterized as a solid solution of $Fe_3O_4$ and $MnFe_2O_4$. Low temperature methods assure crystallization of manganese ferrite in the spinel structure as ferrimagnetic fine particles [R. Bendaoud et al., IEEE Trans. Magnetics, MAG-23: 3869-3873 (1987)].

Notable progress in obtaining monodispersed magnetite and ferrite ($Co^{2+}$, $Ni^{2+}$) particles has been made [T. Sugimoto and E. Matijevic, J. Coll. Interface Sci., 74: 227-243 (1980); H. Tamura and E. Matijevic, J. Coll. Interface Sci., 90: 100-109 (1982); A. E. Regazzoni and E. Matijevic, Corrosion, 38: 212-218 (1982); A. E. Regazzoni and E. Matijevic, Colloids Surf., 6:189-201 (1983); E. Matijevic, J. Coll. Interface Sci., 117: 593-595 (1987); X. J. Fan and E. Matijevic, J. Am. Ceram. Soc., 71; C-60-C-62(1988); International Patent Application WO 88/05357]. In every case, however, the bulk of the magnetic particles in suspension is irreversibly aggregated into large clusters that have a wide range of sizes and shapes. Also, the hydrophobic surface of bare metal oxide particles not only contributes to their agglomeration but also makes them unsuitable for manipulation in aqueous solutions of biological molecules, buffered near pH 7.

Some success in the preparation of polymer-magnetite composite particles of uniform spherical shape has been achieved through the emulsion polymerization of vinyl aromatic monomer in the presence of ferrofluid seed particles which become embedded inside the polymer latex [U.S. Pat. No. 4,358,388 and 4,783,336]. Control over the size of the magnetic latex particles is poor, therefore, resulting in particles with a wide range of sizes and magnetic content. When external surface carboxylic acid groups are introduced, the magnetic latex particles are hydrophilic to some degree but still cannot be dispersed as single particles in buffered aqueous media near pH 7. Coating of these particles by covalent attachment of aminodextran has been carried out to give the particles a hydrophilic shell. These aminodextran-coated particles are stable in an aqueous buffer and have been covalently linked with various monoclonal antibodies (IgG and IgM) for cell depletion.

Uniform polymer-ferrite or -maghemite (magnetic hematite) composite particles have been prepared by crystallizing the magnetic oxide inside uniform spherical and porous polymer particles [International Patent Application WO83/03920; J. Ughelstad et al. in "Microspheres: Medical and Biological Applications," Eds., A. Rembaum and Z. A. Tokes, CRC Press, Inc., Boca Raton, Fla., 1988]. Metal salts were diffused into the pores of the particle and adjustment of pH or oxidation was carried out as required. Alternatively, magnetic porous particles of metal oxide were first prepared and then, the pores were filled and covered with hydrophobic polymer. In both cases it was recognized that an additional hydrophilic polymer coating was required for better specific bead performance.

Solubilized polymers have been used to control the nucleation and growth of various metal particles. The concept of nucleation of metal particles in the domain of the polymer molecule was first described in the formation of cobalt organosols by thermal decomposition of dicobalt octacarbonyl in toluene and other organic solvents with various solubilized polymers [P. H. Hess and P. H. Parker, Jr., J. Appl. Polym. Sci., 10: 1915-1927 (1966)]. The classic protective agent for colloids is gelatin ["The Theory of the Photographic Process," T. H. James, MacMillan Publ. Co., New York, 1977]. Other agents such as the hydrazide of polyacrylic acid and polyethyleneimine-N-alkylacetic acid have been used to obtain stable hydrosols of gold, silver, copper, and platinum metals [H. Thiele and H. S. von Levern, J. Coll. Sci., 20: 679-694 (1965)]. Colloidal dispersions of very small rhodium, iridium, osmium, palladium, platinum, silver, and gold particles in ethanol or methanol with polyvinyl alcohol (PVA) or polyvinylpyrrolidone (PVP) as stabilizer have been prepared [H. Hirai, J. Macromol. Sci. Chem., A12: 1117-1141 (1978); O. Siiman, et al., Chem. Phys. Lett., 100: 163-168 (1983); A. Lepp and O. Siiman, J. Coll. Interface Sci., 105: 325-341 (1985); O. Siiman and W. P. Hsu, J. Chem. Soc., Faraday Trans. 1, 82: 851-867 (1986)]. Functional, soluble polymers have been used to control the formation of colloidal dispersions of selenium and iron [T. W.

Smith and R. A. Cheatham, Macromolecules, 13: 1203-1207 (1980); T. W. Smith and D. Wychick, J. Phys. Chem., 84: 1621-1629 (1980)].

Recently, Hydroxypropyl cellulose was used in the formation and stabilization of monodisperse $TiO_2$ particles by hydrolysis of titanium tetraethoxide in ethanol [J. H. Jean and T. A. Ring, Colloids Surf., 29:273-291 (1988)].

Monodispersed metal ferrite particles have several important applications. They have magnetic properties that are useful for the manufacture of transformers, inductors, audio and video recording heads. Gelatin-coated MnFe or $ZnFe_2O_4$ particles with attached monoclonal antibody represents a completely biodegradable magnetic separation system for biological cells. The particles, coating, and any attached monoclonal antibody can be phagocytosed without killing the cells. Also, gelatin, monoclonal antibody, and cell(s) may be separated from the magnetic particles by enzymatic cleavage of peptide bonds in gelatin, such as, by using trypsin, papain, collagenase and other digestive enzymes. The particles may, furthermore, be used as specific cell surface markers. This invention provides for effective preparation of such monodispersed metal ferrite particles.

SUMMARY OF THE INVENTION

In a method for the preparation of monodispersed colloidal particles of ferrites of manganese, zinc, mixed manganese-zinc, iron, barium, cobalt and nickel, an aqueous metal hydroxide gel is first formed by mixing ferrous and other metal salts in an aqueous gelatin solution with potassium or sodium hydroxide and potassium or sodium nitrate solution, all purged with nitrogen gas. The conversion of the gel to the metal oxide sol is achieved by mild thermal treatment at 90° C. (low temperature) for 4-72 hours, during which nitrate oxidation of ferrous iron occurs. This incubation period also serves to degrade the gelatin as noted by its lower viscosity. Only one type of gelatin, type B or alkali-cured, with a pI range of 4.75 to 5.0 was found optimal for in situ use.

DESCRIPTION OF THE PREFERRED EMBODIMENT

Figure 1:
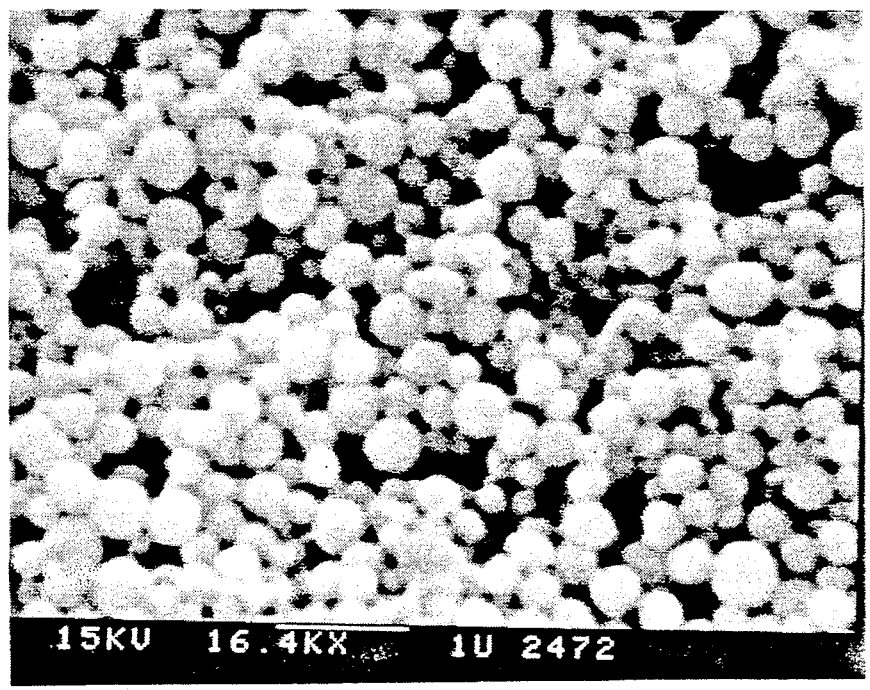
FIG. 1 is a scanning electron micrograph of manganese ferrite particles with white bar indicating a scale of 1 micron length.

Gelatin as a support vehicle for the formation of uniform metal oxide particles has several important roles. First, it serves as a buffer medium to neutralize acid, a product of the heat treatment. Second, gelatin molecules act as loci for the supersaturation of ferrite precursors and the formation an immobilization of ferrite nuclei. They also act as domains to restrict subsequent growth of nuclei and prevent the aggregation of particles. Various amino acid residues (asp, glu, lys, his, met) of gelatin can provide functional groups (carboxylate oxygen, amino nitrogen, imidazole nitrogen, thioether sulfur) through which parts of the reactant amorphous $Fe(OH)_2$ gel and its successors bind to gelatin. The alkali-cured gelatin, that is most successful in promoting the formation of single, uniform particles, contains an excess of carboxylic acid residues, useful in attachment to iron in the $Fe(OH)_2$ gel. Single particles of ferrites are then protected from aggregation by steric repulsion between adsorbed gelatin molecules. Gelatin can also adsorb to the hydrophobic surface of the product, the uncharged metal oxide particles, through its hydrocarbon residues, leaving its hydrophilic residues exposed to the solvent. In subsequent stabilization and use of the magnetic particles, gelatin usage allows chemical linkers to be used in fixing gelatin around particles to produce a stable composite from which gelatin can not be released by physical means. It also allows covalent coupling of a monoclonal antibody, an enzyme, or other proteins to the gelatin-coated particle. It is believed that no other polymer has been successfully substituted for gelatin in its aforementioned functions.

The choice of the metals for ferrite particle formation, involved two principles. Firstly, ferrimagnetic or superparamagnetic particles were preferred over ferromagnetic ones in the size ranges, 0.1 to 1.0 μm in diameter. The former do not possess a permanent magnetic moment but do become magnetized in the presence of a magnetic field. In this way, aggregation possibilities created by the alignment of particle moments are avoided. It is known that ferrites, which have crystal structures of the normal spinel structure type, are ferrimagnetic [A. F. Wells, Structural Inorganiz Chemistry, 5th ed., Clarendon Press, Oxford, 1984]. The requirement for the $M^{2+}$ metal ion to occupy tetrahedral sites in a normal spinel structure is that it gives no crystal field stabilization energy. Metal ion configurations $d^0$ ($Sr^{2+}$, $Ba^{2+}$), high-spin $d^5$ ($Zn^{2+}$), satisfy this condition. Other metal ions ($Fe^{2+}$, $Co^{2+}$, $Ni^{2+}$) form inverse spinel structures in which $M^{2+}$ occupies octahedral sites, $Fe(MFe)O_4$, since these ions have significant octahedral crystal field stabilization energies. The designation "M" refers to a metal.

Secondly, the solubility of the $M(OH)_2$ species in water should be greater than that of $Fe(OH)_2$. Solubility products of representative metal hydroxides at 25° C. are as follows: $2.04 \times 10^{-13}$, Mn $(OH)_2$; $4.79 \times 10^{-17}$, Fe $(OH)_2$; $1.09 \times 10^{-15}$, $Co(OH)_2$; $5.54 \times 10^{-16}$, $Ni(OH)_2$; $7.68 \times 10^{-17}$, $Zn(OH)_2$ [Handbook of Chemistry and Physics, 64th ed., CRC Press, Boca Raton, Fl., 1984, p. B-219]. A value of $Ksp(M(OH)_2) > Ksp (Fe(OH)_2)$ is required so that some $M^{2+}$ will dissolve in aqueous solution and be able to diffuse through the $Fe(OH)_2$ gel and substitute for some of the $Fe^{2+}$ ions. Thus, the more soluble $Mn(OH)_2$, $Co(OH)_2$, and $Ni(OH)_2$ give uniform, submicron ferrite particles in our preparative procedure. The cobalt and nickel ferrites showed clustering of particles similar to that of ferromagnetic magnetite particles after multiple washings and magnetic separations. Ferrimagnetic manganese, zinc and mixed manganese-zinc ferrites showed little or no tendency to aggregate. Also, $Zn(OH)_2$ is almost as insoluble as $Fe(OH)_2$ and $Zn(OH)_2$ is amphoteric, so that stable zincate ions, $ZnO_2^-$ are formed in basic solution. Very small amounts of magnetic material were obtained by this procedure with zinc. However, a 1:1 manganese-to-zinc sulfate mixture gave uniform magnetic ferrite particles in good yield. In addition, $Ba^{2+}$, which forms a very soluble hydroxide produced uniform submicron magnetic ferrite particles.

The following solutions of reagent grade metal salt s in double distilled water (DDW) were prepared: 5 M KOH, 2 M $KNO_3$, 1 M $FeSO_4$, 1 M $MnSO_4$, 0.25 M $ZnSO_4$, 1 M $Co(NO_3)_2$, 1 M $Ni(NO_3)_2$, 0.1 M $Ba(NO_3)_2$, and 1 M $FeCl_2$. All stock solutions except the KOH solution, were filtered through 0.2 μm cellulose nitrate filters. The $FeSO_4$ and $FeCl_2$ solutions were purged with nitrogen gas for 10 minutes each time they were used and not stored for more than one week. Gelatin, type B, 225 Bloom, bovine skin, was prepared freshly as a 2% solution in double distilled water and purged with nitrogen gas for 10 minutes.

Example 1

Preparation of Magnetite particles 10 mmol $KNO_3$ (5 mL) solution, 12.5 mmol KOH (2.5 mL) solution, and 11.25 mL DDW were mixed and purged with $N_2$ gas for 10 minutes (solution A). 6.25 mmol $FeSO_4$ (6.25 mL) solution and 25 mL 2% gelatin solution was then added to solution A in a Pyrex bottle, mixed, swept with $N_2$ gas, capped tightly, and placed undisturbed in oven at 90° C. for 4 hours. After the suspension of black magnetite particles reached room temperature, it was sonicated for ½ hour and the particles were then washed five times with 1% gelatin solution by magnetic separation and redispersion in gelatin solution. The suspension was sonicated for 5 minutes between each wash.

Microscopic examination of the particles at 1000× magnification showed almost exclusively single, spherical particles of about 0.5 μm diameter. If the molar ratio of $Fe^{2+}:OH^{-1}$ was changed from 1:2 to 1:1 by using 6.25 mmol KOH (1.25 mL) in the procedure, then similar black magnetite particles aggregated into small clusters with some single particles were obtained. When the $KNO_3$ solution was pre-mixed with the $FeSO_4$ solution and other steps were unchanged, very small reddish-brown particles in stringy aggregates were produced. Therefore, the first procedure was adopted as the standard one in subsequent experiments.

Other types of gelatin such as type B, 60 Bloom; type A, 175 Bloom; and type A, 300 Bloom did not perform. More and larger aggregates of magnetite particles were formed in each case. Various PVA polymers in molecular weight (MW) range 3,000 to 106,000 gave irregular large black aggregates of magnetite particles which could not be dispersed. Similar results were observed with polyacrylamide ($5-6 \times 10^6$ MW) and sodium dodecyl sulfate. Polyacrylic acid (2K and 5K MW) and dextran (100K and 500K MW) gave large brown crystalites which were only weakly magnetic; whereas, polyacrylic acid and dextran of higher molecular weight gave no magnetic material. Also, polystyrene sulfonic acid, PVP, and sulfonated casein gave no magnetic material.

Example 2

Preparation of Metal Ferrites

In trials with other metals, namely, $Mn^{2+}$, $Zn^2$, $Co^{2+}$, $Ni^{2+}$, and $(M^{2+})$, the molar ratio of $M^{2+}:Fe^{2+}$ kept at 1:2, but nitrate instead of sulfate salts of $Co^{2+}$ and $Ni^{2+}$ were used. The total metal-to hydroxide molar ratio was maintained at 1:2; but, the relative $KNO_3$ to total metal and $KNO_3$ to KOH molar ratios were altered. In preparing the mixed Mn:Zn ferrite, a 1:1 molar ratio of manganese sulfate to zinc sulfate and the same total molar amount of nonferrous metal ions were used.

10 mmol $KNO_3$ (5 mL) solution, 18.75 mmol KOH (3.75 mL), and 6.875 mL DDW were mixed and purged with $N_2$ gas for 10 minutes (solution C). 6.25 mmol $FeSO_4$ (6.25 mL) solution, 3.125 mmol $Co(NO_3)_2$ (3.125 mL) solution, and 25 mL 2% gelatin solution were mixed and purged with $N_2$ gas for 10 minutes (solution D). Solution D was added to solution C in a Pyrex bottle, mixed, swept with $N_2$ gas, capped tightly, and placed undisturbed in an oven at 90° C. for 5 hours. After the suspension of brown particles had reached room temperature, it was sonicated for ½ hour and the particles were then washed 5 times with 1% gelatin solution by magnetic separation and redispersion in gelatin solution. The suspension was sonicated for 5 minutes between each wash.

Cobalt and nickel ferrite particles of about 0.1 and 0.2 μm in diameter and of spherical shape were formed in large, loosely-held brown aggregates. Zinc gave low yields of light brown magnetic material (<0.2 μm diameter) even after 72 hours of heat treatment. Dark brown manganese ferrite particles of uniform, spherical shape and 0.3 μm diameter were obtained as single particles in 83-88% yields. Similar light brown manganese-zinc ferrite particles were produced in 49-55% yield after 72 hours of heat treatment at 90° C. For barium, the procedure had to be modified since $BaSO_4$ is insoluble in water. Thus, 6.25 mmol FeCl (6.25 mL) solution, 0.5 mmol $Ba(NO_3)_2$ (5.0 mL) solution, and 25 mL 2% gelatin solution were mixed and purged with $N_2$ gas for 10 minutes (solution D). Solution C and the remainder of the ferrite preparation procedure was unchanged except 10 mmol KOH solution (2 mL) was used and the heat treatment was continued for 20 hours. Black barium ferrite particles of uniform non-spherical shape with a 0.2 μm diameter were produced.

Because of their favorable magnetic, size and shape properties, manganese ferrite particles were also prepared at larger scales and analyzed further by physical means. Concentrations of reactants were scaled up linearly at 250 and 500 mL total volume levels. For the 250 mL-scale, the heat treatment at 90° C. was still for 5 hours, but it was increased to 48 hr to achieve better gel-to-sol conversion on the 500 mL scale. Percentage yields based on a 2:1 molar ratio of $FeSO_4:MnFe_2O_4$ were 83% at the 250 mL scale and 84% at the 500 mL scale. The particles were washed exhaustively with DDW and then dried at 110° C. and weighed to constant weight. Elemental analyses were obtained on a 250 mL scale preparation as follows: Calculated for $MnFe_2O_4$ Mn, 23.82%; Fe, 48.43%; observed: Mn, 20.01%; Fe, 49.99%. Duplicate pycnometer measurements of density for manganese ferrite particles by displacement of DDW gave 4.24 and 4.23 g/cc. A scanning electron micrograph (FIG. 1) of manganese ferrite particles showed particles of spherical shape and uniform size. The mean diameter for 414 particles was 0.29(.08) μm.

Figure 2:
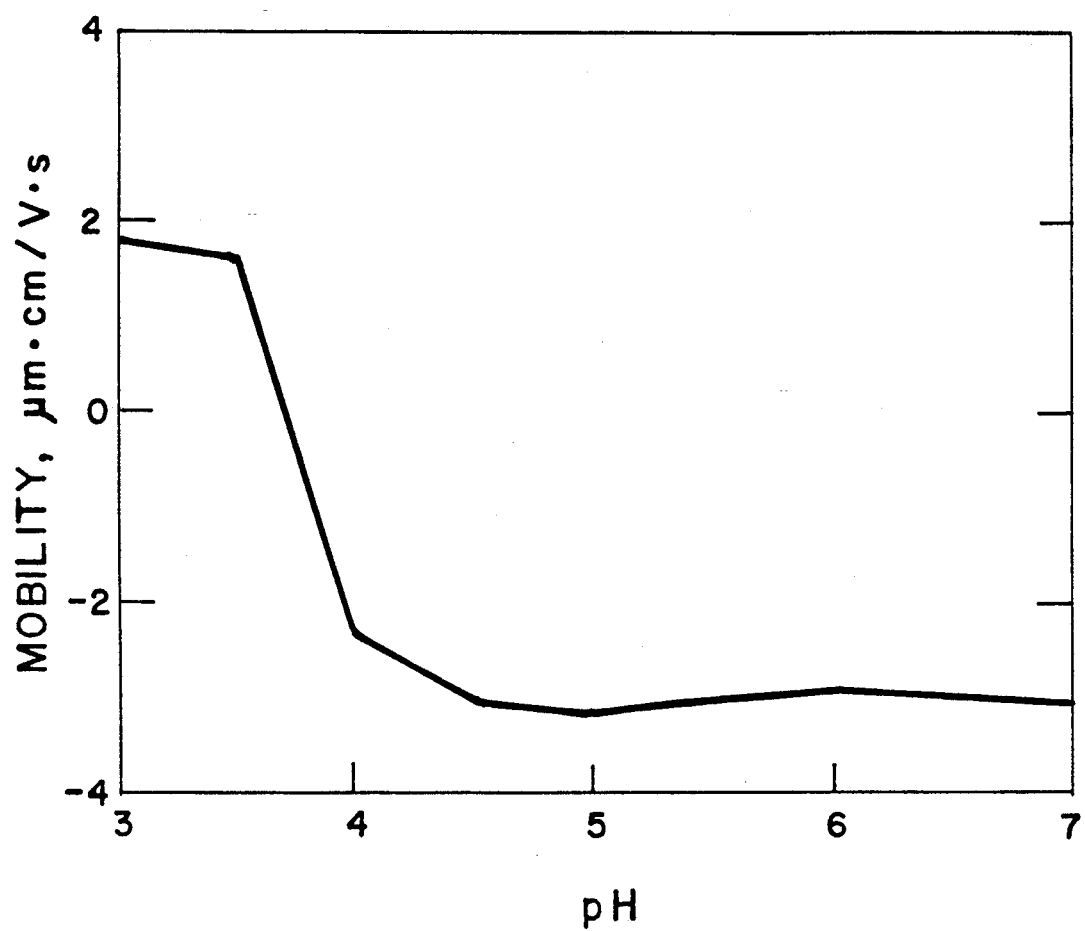
FIG. 2 is a graph of mobility versus pH for bare manganese ferrite particles in 1 mM aqueous sodium nitrate suspension at 25° C.

The specific surface ($S_w$) for manganese ferrite particles is then 4.89 m²/g. This compares favorably with magnetite embedded polystyrene latex beads as follows: (1) 0.7 μm, 41% magnetite, 1.56 g/cc gives Sw=5.50 m²/g; (2) 0.098 μm, 23% magnetite, 1.28 g/cc gives 4.78 m²/g. The most recent porous ferrite hydrophobic polymer-filled and covered beads give an $S_w$ range of 3-5 m²/g. The electrophoretic mobility of bare manganese ferrite particles in 1 mM aqueous nitrate at 25° C., measured as a function of pH (adjusted with aqueous sodium hydroxide or nitric acid) on the Coulter DELSA 440, is shown in FIG. 2. An isoelectric point of about 3.7 for the colloidal particles and a zeta potential of $-65$ mV at pH 7 was obtained.

Elemental analyses were also obtained for manganese-zinc ferrite: calculated; for $Mn_{0.5}Zn_{0.5}Fe_2O_4$ Mn, 11.65%; Zn, 13.86%; Fe, 47.36%; observed: Mn, 10.86%; Zn, 11.61%; Fe, 47.12%. The density of manganese-zinc ferrite particles was 4.13 and 4.20 g/cc in duplicate measurements. The specific surface for manganese-zinc ferrite particles is 4.97 $m^2/g$.

The method embodying the invention contemplates substituting a mixture of sodium hydroxide and sodium nitrate for the potassium hydroxide and potassium nitrate mixture. Also, divalent metal nitrates, i.e., of $Co^{2+}$, $Ni^{2+}$, $Zn^{2+}$ and $Ba^{2+}$ can be replaced by divalent metal chlorides and divalent metal sulfates except for the divalent metal $Ba^{2+}$ which forms an insoluble barium sulfate compound. The divalent metal sulfates of $Zn^{2+}$, $Zn^{2+}$, and $Fe^{2+}$ can be replaced by divalent metal chlorides and nitrates except for ferrous nitrate which is unstable because of subsequent oxidation to form ferric nitrate.

The relatively low temperature employed in practicing the invention can vary in the range of 85°-95° C. Also, the time period for nitrogen gas purging may be varied within appropriate limits without adversely affecting practicing the invention. Also, the percentage rating of the gelatin solution may vary within the approximate range of 0.8% to 2.0%.

The colloidal particles prepared by the herein invention are monodisperse with a ferrite structure and a mean particle diameter of approximately 0.1 to 1.0 microns. The Mn(II) ferrite particles contain approximately 17 to 21 percent by weight of manganese ions. The Mn(II), Zn(II), mixed Mn(II)-Zn(II) and Ba(II) ferrite particles have a ferrimagnetic response to a magnetic field, i.e., possess no magnetic memory, while magnetite and Co(II) and Ni(II) ferrite particles have a ferromagnetic response.

The Mn(II) and mixed Mn(II)-Zn(II) particles have a significantly lower density of 4.2 g/cc than the 5.2 g/cc density of the magnetite particles whereby submicron particles are made more buoyant in aqueous suspensions.

The Mn(II), Zn(II) and mixed Mn(II)-Zn(II) particles have surfaces which are less hydrophobic than the surfaces of a magnetite particle which have an isoelectric point of 6.7 as compared to the isoelectric point of 3.7 of Mn(II) ferrite particles. The Mn(II) ferrite particles are more stable in aqueous suspension in proximity to pH 7 due to electrostatic repulsion between negatively charged particles. The Mn(II) and mixed Mn(II)-Zn(II) ferrite particles have a high specific surface of 5 $m^2/g$.

CONTINUATION-IN-PART DISCLOSURE

In general, dextrans of varying molecular weight were not suitable substitutes for the type B, 225 Bloom, bovine skin gelatin used in the preparation of magnetite and ferrite particles as described above, However, aminodextran derivatives, when used according to the procedure described in Example 2 above, could substitute for gelatin in the preparation of manganese ferrite particles. It was determined that the protecting ability of aminodextrans having both hydroxyl and amino functional groups was less than that of gelatin having both acidic and basic groups. As a result, the magnetic product which was obtained formed some small clusters of single particles. The aggregation could be minimized by using lesser amounts of metal salts and hydroxide relative to the aminodextran in the reaction solutions. The degree on amino substitution on the dextran does not appear to affect the results.

SUMMARY OF THE INVENTION

In a method for the preparation of monodispersed colloidal particles of manganese containing ferrites, an aqueous metal hydroxide gel is first formed by mixing ferrous and other metal salts in an aqueous aminodextran solution with potassium or sodium hydroxide and potassium or sodium nitrate solution, all purged with nitrogen gas. The conversion of the gel to the metal oxide sol is achieved by mild thermal treatment at 90° C., a so-called (low temperature treatment for 4-72 hours. The animodextrans used according to the invention contain from 15 to 80 mole per cent polyaminoalkyl groups attached to dextran. The preferred aminodextrans contain from 15 to 80 mole per cent 1,3-diaminopropyl groups attached to dextran.

DETAILED DESCRIPTION OF THE INVENTION

Example 3

Preparation of Metal Ferrites Using Aminodextran

In a typical preparation, 1 mmol of $KNO_3$ (0.5 of 2 M) solution 1.875 mmol KOH (0.375 mL of 5 M) solution and 18.78 ml of doubly distilled water were mixed and purged with nitrogen gas for 10 minutes to prepare solution E. 0.625 mmol $FeSO_4$ (0.625 mL of 1 M) solution, 0.3125 mmol $MnSO_4$ (0.3125 mL of 1) solution and 29.4 mL of 3.4% w/v aminodextran solution were mixed and purged with nitrogen gas for 10 minutes to prepare solution F. solution F was then added to solution E in a 100 ml Pyrex bottle, mixed, swept with nitrogen gas, capped tightly and placed undisturbed in an oven at about 90° C. for about 18 hours. The resulting suspension of dark brown particles was removed from the oven, cooled to ambient temperature and sonicated for about 0.5 hour. The particles were then washed five times with 2% w/v aminodextran solution, using magnetic separation and redispersion by sonication for 5 minutes with each wash solution. Microscopic examination of the particles with a 100× objective and a 10× eyepiece using a calibrated reticule showed single, spherical particles about 0.3 µm diameter. There were a few small clusters of less than ten primary particles. The particles were generally monodispersed, had a ferrite structure and had a mean particle diameter in the range of about 0.1 to about 1.0 microns.

Aminodextrans having alkyl groups of varying length connecting the amine function to the dextran structure may be used according to the invention, The preferred aminodextran is 1,3-diaminopropyldextran. 1,3-diaminopropyldextran was prepared by a method similar to that outlined by D. Hicks et al., Invest. Opthalmol. Vis. Sci., 23: 1002-1013 (1985), for diaminoethane-derivatized dextran TIO. Accordingly, 1,3-diaminopropyldextran was prepared as follows. A solution of 20 g of dextran T-2M (Sigma, 0.123 mol units) in 150 mL of 50 mM potassium acetate, pH 6.5, was mixed with a solution of 2.14 g of sodium periodate (0.01 mol) in 25 mL of distilled water for 1.5 hours. The resulting colorless oxidized dextran solution was dialyzed against 10 L of distilled water and then reacted with 20 mL of 1,3-diaminopropane (0.238 mol) in 20 mL of distilled water at pH 8.7 (pH adjustment with glacial acetic acid). After 2 hours, 0.8 g sodium borohydride in 10 mL of 0.1 mM sodium hydroxide solution was added to stabilize the yellow to brown Schiff's base derivative. The resulting solution was dialyzed against distilled water to a conductivity of about 3-4 μohm-cm and filtered through a 0.2 μM cellulose nitrate filter to give a very pale yellow aminodextran concentrate of 34 mg/mL based on 100% yield. Aminodextrans having a higher degrees of substitution can be prepared in the same manner. For example, aminodextrans having two-to-five fold greater substitution of dextran T-2M were prepared by the above procedure using two-to-five greater molar amounts of sodium periodate, 1,3-diaminopropane and sodium borohydride.

We claim:

1. A method of making colloidal ferrite particles of uniform size and shape comprising:
   A. mixing a first solution of potassium nitrate and potassium hydroxide or sodium nitrate and sodium hydroxide, respectively, which has been nitrogen gas purged and a
   B. second solution of ferrous salt, divalent metal salt and an aminodextran solution which second solution has been nitrogen purged;
   C. sweeping the aminodextran- metal hydroxide mixture of the two solutions with nitrogen gas and ripening same to form a ferrite hydrosol at a predetermined low temperature for a selected period of time;
   D. washing the hydrosol with said aminodextran solution by magnetic separation and redispersion, whereby to form separate single metal ferrite particles coated with an aminodextran.

2. The method of claim 1 in which the metal ion of said divalent metal salt is the $Fe^{2+}$ ion.

3. The method of claim 2 in which said ferrous salt can be either a chloride or sulfate salt.

4. The method of claim 1 in which the metal ion of said divalent metal salt is the $Mn^{2-}$ ion.

5. The method of claim 1 in which said divalent metal salt is selected from the group consisting of a metal chloride, metal sulfate and metal nitrate salt, except that when barium is said divalent metal or is present in any of the steps A to C, said divalent metal salt is a metal chloride or a metal nitrate salt.

6. The method of claim 5 in which said divalent metal salt is selected from a mixture of metal chloride, metal sulfate and metal nitrate salts.

7. A colloidal ferrite particle produced by the method of claims 1 or 2.

8. Colloidal particles which are monodispersed having a ferrite structure and a mean particle diameter of approximately 0.1 to 1.0 microns, said particles including the divalent metal ion manganese(II)) and characterized as being well-defined and of uniform size and shape.

9. The colloidal particles of claim 8 in which ferrite particles of manganese(II) display a ferrimagnetic response to a magnetic field.

* * * * *

UNITED STATES PATENT AND TRADEMARK OFFICE
CERTIFICATE OF CORRECTION

PATENT NO. : 5,240,640
DATED : August 31, 1993
INVENTOR(S) : Olavi Siiman and Alexander Burshteyn Page 1 of 2

It is certified that error appears in the above-indentified patent and that said Letters Patent is hereby corrected as shown below:

Column 1, line 68, change "WO 88/053S7" to --WO 88/05337--;

Column 3, line 13, change "MnFe" to --$MnFe_2O_4$--;

Column 4, line 33, change "$d^5$ ($Zn^{2+}$)" to --$d^5$ ($Mn^{2+}$) and $d^{10}$ ($Zn^{2+}$)--;

line 59, change "$ZnO_2-$" to --$ZnO_2^{2-}$--;

Column 5, line 58, change "kept" to --was kept--;

Column 6, line 24, change "FeCl" to --$FeCl_2$--;

lines 47-48, change "$MnFe_2O_4$ Mn" to --$MnFe_2O_4$: Mn--;

Column 7, lines 2, change "$Mn_{0.5}Zn_{0.5}Fe_2O_4$ Mn" to --$Mn_{0.5}Zn_{0.5}Fe_2O_4$: Mn--;

line 16, change "$Zn^{2+}$, $Zn^{2+}$" to --$Mn^{2+}$, $Zn^{2+}$--;

Column 8, line 26, change "solution 1.875" to --solution, 1.875--;

line 33, change "F. solution" to --F. Solution--;

line 57, change "TIO" to --T10--;

UNITED STATES PATENT AND TRADEMARK OFFICE
CERTIFICATE OF CORRECTION

PATENT NO. : 5,240,640
DATED : August 31, 1993
INVENTOR(S) : Olavi Siiman and Alexander Burshteyn It is certified that error appears in the above-indentified patent and that said Letters Patent is hereby corrected as shown below:

Column 8, line 59, after "mol" insert --sugar--.

Signed and Sealed this

Eighth Day of March, 1994

Attest:

BRUCE LEHMAN

Attesting Officer   Commissioner of Patents and Trademarks